(12) United States Patent
Coffey et al.

(10) Patent No.: US 12,372,516 B2
(45) Date of Patent: Jul. 29, 2025

(54) METHODS AND COMPOSITIONS FOR LATERAL FLOW ANALYTE ASSAYS

(71) Applicant: IVD VISION, LLC, Carlsbad, CA (US)

(72) Inventors: William Patrick Coffey, Carlsbad, CA (US); Gregory Reneff, Carlsbad, CA (US); Ezra John Spencer, Carlsbad, CA (US)

(73) Assignee: IVD VISION, LLC, Carlsbad, CA (US)

( * ) Notice: Subject to any disclaimer, the term of this patent is extended or adjusted under 35 U.S.C. 154(b) by 618 days.

(21) Appl. No.: 17/778,332

(22) PCT Filed: Nov. 19, 2020

(86) PCT No.: PCT/US2020/061344
§ 371 (c)(1),
(2) Date: May 19, 2022

(87) PCT Pub. No.: WO2021/102175
PCT Pub. Date: May 27, 2021

(65) Prior Publication Data
US 2023/0003722 A1    Jan. 5, 2023

Related U.S. Application Data

(60) Provisional application No. 62/937,652, filed on Nov. 19, 2019.

(51) Int. Cl.
*G01N 33/52*    (2006.01)
*B01L 3/00*     (2006.01)
(Continued)

(52) U.S. Cl.
CPC ............ *G01N 33/52* (2013.01); *B01L 3/5023* (2013.01); *G01N 21/78* (2013.01);
(Continued)

(58) Field of Classification Search
CPC ........... B01L 2200/12; B01L 2200/148; B01L 2300/0654; B01L 2300/0825;
(Continued)

(56) References Cited

U.S. PATENT DOCUMENTS

| 4,703,017 A | 10/1987 | Campbell et al. |
| 4,743,560 A | 5/1988 | Campbell et al. |

(Continued)

FOREIGN PATENT DOCUMENTS

| EP | 0653625 A1 | 5/1995 |
| EP | 0833145 A1 | 4/1998 |
| GB | 2569554 A1 | 6/2019 |

OTHER PUBLICATIONS

International Search Report and Written Opinion issued in PCT/US2020/061344 on Mar. 26, 2021 (11 pages).

(Continued)

*Primary Examiner* — Jennifer Wecker
*Assistant Examiner* — Jonathan Bortoli
(74) *Attorney, Agent, or Firm* — Michael A. Whittaker (57) ABSTRACT

It is an object of the present invention to provide improved lateral flow test devices that can provide sensitive and accurate quantitative test results, and methods for the manufacture thereof.

16 Claims, 7 Drawing Sheets

(51) Int. Cl.
*G01N 21/77* (2006.01)
*G01N 21/78* (2006.01)
*G01N 33/543* (2006.01)

(52) U.S. Cl.
CPC .... *G01N 33/54388* (2021.08); *B01L 2200/12* (2013.01); *B01L 2200/148* (2013.01); *B01L 2300/0654* (2013.01); *B01L 2300/0825* (2013.01); *G01N 2021/7759* (2013.01)

(58) Field of Classification Search
CPC ... B01L 3/5023; A61K 31/4166; A61K 47/10; A61K 47/14; A61K 47/26; A61K 9/0053; A61K 9/08; G01N 2021/7759; G01N 21/78; G01N 21/8483; G01N 33/52; G01N 33/54388; G01N 33/558
See application file for complete search history.

(56) References Cited

U.S. PATENT DOCUMENTS

| | | | |
|---|---|---|---|
| 4,942,522 A | 7/1990 | Wilkie et al. | |
| 4,956,302 A | 9/1990 | Gordon et al. | |
| 5,028,139 A * | 7/1991 | Kramer | G01N 21/474 356/446 |
| 5,073,484 A | 12/1991 | Swanson et al. | |
| 5,120,643 A | 6/1992 | Ching et al. | |
| 5,252,496 A | 10/1993 | Kang et al. | |
| 5,559,041 A | 9/1996 | Kang et al. | |
| 5,580,794 A | 12/1996 | Allen | |
| 5,591,645 A | 1/1997 | Rosenstein | |
| 5,602,040 A | 2/1997 | May et al. | |
| 5,622,871 A | 4/1997 | May et al. | |
| 5,654,162 A | 8/1997 | Guire et al. | |
| 5,656,448 A | 8/1997 | Kang et al. | |
| 5,656,503 A | 8/1997 | May et al. | |
| 5,714,389 A | 2/1998 | Charlton et al. | |
| 5,728,587 A | 3/1998 | Kang et al. | |
| 5,989,921 A | 11/1999 | Charlton et al. | |
| 6,020,147 A | 2/2000 | Guire et al. | |
| 6,027,943 A | 2/2000 | Kang et al. | |
| 6,187,598 B1 | 2/2001 | May et al. | |
| 6,228,660 B1 | 5/2001 | May et al. | |
| 6,352,862 B1 | 3/2002 | Davis et al. | |
| 6,394,952 B1 | 5/2002 | Anderson et al. | |
| 6,485,982 B1 | 11/2002 | Charlton | |
| 6,506,612 B2 | 1/2003 | Kang et al. | |
| 6,534,320 B2 | 3/2003 | Ching et al. | |
| 6,541,277 B1 | 4/2003 | Kang et al. | |
| RE38,430 E | 2/2004 | Rosenstein | |
| 6,737,277 B1 | 5/2004 | Kang et al. | |
| 6,818,455 B2 | 11/2004 | May et al. | |
| 7,141,212 B2 | 11/2006 | Catt et al. | |
| 7,763,454 B2 | 7/2010 | Nazareth et al. | |
| 9,222,875 B2 | 12/2015 | Egan et al. | |
| 2001/0008774 A1 | 7/2001 | May et al. | |
| 2003/0143755 A1 | 7/2003 | Davis et al. | |
| 2003/0207465 A1 | 11/2003 | Davis et al. | |
| 2003/0219908 A1 | 11/2003 | Davis et al. | |
| 2005/0244986 A1 | 11/2005 | May et al. | |
| 2006/0008896 A1 | 1/2006 | Nazareth et al. | |
| 2006/0040405 A1 | 2/2006 | Charlton et al. | |
| 2006/0240541 A1* | 10/2006 | Petruno | G01N 33/54388 435/287.2 |
| 2011/0223673 A1* | 9/2011 | Profitt | G01N 21/8483 436/164 |
| 2013/0280696 A1 | 10/2013 | Millenson et al. | |
| 2018/0246038 A1* | 8/2018 | Hunter | G01N 21/274 |
| 2020/0072722 A1* | 3/2020 | Ryu | G01N 15/06 |

OTHER PUBLICATIONS

International Search Report issued in PCT/US2020/061344 dated Mar. 26, 2021 (11 pages).
International Preliminary Report on Patentability issued in PCT/US2020/061344 dated Jun. 2, 2022 (8 pages).
Extended European Search Report issued in EP 20890587.7 dated Feb. 6, 2024 (14 pages).

* cited by examiner

METHODS AND COMPOSITIONS FOR LATERAL FLOW ANALYTE ASSAYS

CROSS-REFERENCE TO RELATED APPLICATIONS

The present invention is filed under 35 U.S.C. § 371 as the U.S. national phase of International Application No. PCT/US2020/061344, filed Nov. 19, 2020, which designated the U.S. and claims the benefit of priority to U.S. Provisional Application No. 62/937,652, filed Nov. 19, 2019, the contents of each of which are incorporated herein by reference.

BACKGROUND OF THE INVENTION

The following discussion of the background of the invention is merely provided to aid the reader in understanding the invention and is not admitted to describe or constitute prior art to the present invention.

Lateral flow assay devices are widely used in many different areas of analytical chemistry and medicine, and have become the format of choice for tests such as immunoassays which are to be performed by relatively untrained users in a rapid testing protocol. Typically, the devices and methods allow for application of a sample to a lateral flow matrix. The sample flows along the lateral flow matrix, and one or more analyte components to be detected in the sample react with at least one reagent which is provided in or added to the lateral flow matrix. At least one reagent is typically immobilized in the device for reaction with the analyte component to be detected or a reagent thereof, and labels are typically employed to provide a detectable signal that can be used to measure the extent of reaction with an immobilized reagent. See, e.g., U.S. patents and patent application publications: U.S. Pat. Nos. 5,602,040; 5,622,871; 5,656,503; 6,187,598; 6,228,660; 6,818,455; 2001/0008774; 2005/0244986; U.S. Pat. No. 6,352,862; 2003/0207465; 2003/0143755; 2003/0219908; U.S. Pat. Nos. 5,714,389; 5,989,921; 6,485,982; Ser. No. 11/035,047; U.S. Pat. Nos. 5,656,448; 5,559,041; 5,252,496; 5,728,587; 6,027,943; 6,506,612; 6,541,277; 6,737,277 B1; 5,073,484; 5,654,162; 6,020,147; 4,956,302; 5,120,643; 6,534,320; 4,942,522; 4,703,017; 4,743,560; 5,591,645; and RE 38,430.

Lateral flow assay devices may comprise a housing having a sample port and a result window downstream of the sample port, and, optionally, a control window separate from the result window. The sample port is adapted to receive a quantity of liquid buffer or sample applied thereto which traverses a lateral flow path via a bibulous matrix or capillary material within the housing, extending from the sample port to a downstream location. The housing may be formed of any suitable material, an example of which comprises molded plastic, and is preferably sufficiently rigid to provide support and stability for the lateral flow path or paths housed therein.

Electronic readers for use in combination with lateral flow assay devices are also known. These readers measure the detectable label that is used for determining the concentration and/or amount of analyte in a fluid sample. EP653625 discloses such a device which uses an optical method in order to determine the result. Typically, an assay test strip is inserted into a reader such that the strip is aligned with optics provided by reader. Light from a source of electromagnetic radiation, such as a light emitting diode (LED), laser, etc., is directed toward the test strip at the detection (and optionally control) zone and reflected or transmitted or fluoresced light is detected by a photodetector in the reader. In certain readers, the reader will have more than one LED, and a corresponding photodetector is provided for each of the plurality of LED's.

An important consideration in assay reading devices of this type is the requirement that the assay reader and the test strip are carefully aligned. This is because the visible signal formed in the detection zone (and the control zone, if present) is fairly narrow (about 1 mm wide), so a small displacement of the detection or control zone relative to the respective photodetector may significantly affect the reading made by the photodetector. In addition, it is generally important that the photodetector is as close as possible to the test strip, because the amount of light which is 'captured' by the photodiode is fairly small, and the signal intensity normally obeys the inverse square law, so that it diminishes rapidly as the separation between the test strip and the photodetector increases.

In some cases, the reader and the lateral flow test device are provided as a single device. For example, U.S. Pat. No. 5,580,794 discloses a fully disposable integrated assay reader and lateral flow assay test strip, whereby optics present in the reader enable the result to be determined optically using reflectance measurements.

An alternative solution is taught by EP 0833145, which discloses a test strip and assay result reader combination, wherein the assay result reading device can be successfully triggered to make a reading only when there is a precise three-dimensional fit between the test strip and the reader, thereby ensuring the correct alignment has been obtained.

Many lateral flow test devices are limited to answering yes/no questions such as those concerning pregnancy or influenza. That is, below a certain threshold of analyte concentration in the original sample, no detectable signal is perceived, and the result is interpreted to be negative. Above the threshold, the signal is detected, and a positive result is determined. Advantages of these tests are that they are relatively simple to perform and interpret, and relatively inexpensive to fabricate. However, to obtain quantitative or even semi-quantitative results, more sophisticated instruments are employed. Many important tests require a quantitative result, which is not always achievable in a lateral flow assay format.

SUMMARY OF THE INVENTION

It is an object of the present invention to provide improved lateral flow test devices that can provide sensitive and accurate quantitative test results, and methods for the manufacture thereof.

In a first aspect, the invention relates to lateral flow analyte test devices that contain an integrated electronic reader. These devices comprise:
  (a) a test strip comprising
    a first bibulous material forming a sample receiving region,
    a second bibulous material forming an absorbent region, and
    a porous membrane fluidly connected to the first bibulous material at a proximal end of the porous membrane, and fluidly connected to the second bibulous material at a distal end of the porous membrane, wherein the proximal and distal ends of the porous membrane define a flow path such that a sample applied to the sample receiving region traverses the porous membrane from the proximal end thereof to the distal end thereof, wherein a longitudinal axis is defined from the proximal end of the porous membrane to the distal end of the porous membrane, and a width axis is defined perpendicular to the longitudinal axis from a first lateral edge of the porous membrane to a second lateral edge of the porous membrane, wherein the dimension of the porous membrane along its longitudinal axis is greater than the dimension of the porous membrane along its width axis, and wherein the porous membrane comprises at least one test zone comprising one or more reagents configured to bind for detection at least one analyte of interest from the sample immobilized at the at least one test zone, the test zone occupying an area of the porous membrane defined by a width ($W_T$) along the width axis of the porous membrane and a length ($L_T$) along the longitudinal axis of the porous membrane;

(b) a generally rigid base which supports the test strip;

(c) a circuit board comprising at least one light source configured to illuminate the at/at least one test zone with electromagnetic radiation, and at least one photodetector configured to detect an optical signal from the test zone resulting from illumination of the test zone by the electromagnetic radiation;

(d) a circuit board support configured to position the at least one light source above the test zone at a height $h_1$ and at a location that is lateral to the width axis of the porous membrane, and to position the at least one photodetector above the at least one test zone at a height $h_2$ and at a location that is approximately centered on the width axis of the porous membrane, wherein the circuit board support comprises an elongate first aperture having a first end proximal to the light source and a second end proximal to the at least one test zone, wherein the height $h_1$ and the dimensions of the elongate first aperture are configured and arranged such that electromagnetic radiation from the light source illuminates the at least one test zone at an angle of incidence θ, measured relative to a surface normal from the porous membrane, that is between about 40° and about 10°, and a second aperture between the at least one test zone and the at least one photodetector, wherein the height $h_2$ and the dimensions of the second aperture are configured and arranged such that that the angle of view of the photodetector samples an area ($S_A$) of the porous membrane that comprises the test zone that is no more than twice the area occupied by the test zone;

(e) a processing component operably connected to the at least one light source and the at least one photodetector to (i) control the illumination of the test zone by the light source, (ii) receive an electrical signal from the photodetector resulting from the optical signal, and (iii) convert the electrical signal into an assay result indicative of the presence or amount of the analyte of interest in the sample; and (f) a display component operably connected to the processing component to display the assay result.

In certain embodiments, the processing component processes the electrical signal resulting from the optical signal detected from the test zone by performing a calculation to arrive at a processed signal. It is this processed signal which is then used to determine the assay result. In preferred embodiments, the processed signal is defined by the equation 1−[(total optical signal measured)−(offset signal)]/ [(reference signal)−(offset signal)], wherein the total optical signal is defined by the optical signal measured following performance of the test for the at least one analyte of interest on the lateral flow analyte test device;

the reference signal is defined by an optical signal measured from a corresponding unreacted test device;

and wherein the offset signal is defined by an optical signal measured from a corresponding test device in which the porous membrane is replaced with a material that absorbs at least 90% of the electromagnetic radiation emitted from the light source.

In certain embodiments, $S_A$ is defined by a sampling width ($W_S$) that is no more than 50% larger than $W_T$, and a sampling length ($L_S$) that is no more than 50% larger than $L_T$.

In certain embodiments, $S_A$ is defined by a sampling width ($W_S$) that is less than 75% of $W_T$, and a sampling length ($L_S$) that is no more than 10% larger than $L_T$.

The reference signal is typically measured at run time prior to sample flowing down the membrane. That reference signal may then be stored in a memory component on the test device and used to determine the scaled absorbance of the test or control signal per the equation above. The reference signal may also be generated at the time of production and stored in the memory unit. The offset signal may be measured at the point of manufacture of the lateral flow analyte test device in a device which is physically similar or identical to the lateral flow analyte test device, but in which the porous membrane is replaced by the material that absorbs at least 90% of the electromagnetic radiation. Again, this offset signal may then be stored in a memory component of each test device in the manufacturing lot for access by the processing component of each test device at the time a particular test device is used by an end user.

The lateral flow analyte test devices of the present invention may provide a binary (threshold) result, a semi-quantitative result (meaning that the measurement of a quantity of material is accurate to within a range of values), or most preferably a quantitative result.

In certain embodiments the presence or amount of the at least one analyte of interest in the sample is measured by measuring an amount of reflectance by the material at the test zone of the electromagnetic radiation emitted from the light source, by measuring an amount of absorbance by the material at the test zone of the electromagnetic radiation emitted from the light source, by fluorescence of the material at the test zone excited by the electromagnetic radiation emitted from the light source, etc., depending on the type of detectable label used in the device. Suitable detectable labels known in the art include, but are not limited to, colloidal gold, fluorescent latex nanoparticles, quantum dots, europium chelates, etc.

The lateral flow analyte test devices can be configured to perform competitive or sandwich assay formats. Detectable species (e.g., antibodies to the analyte, a receptor for the analyte, complimentary oligonucleotides, or a molecule that competes with an analyte for binding to an analyte) can be noncovalently or covalently bound or attached to the detectable label of choice. In certain embodiments, the first bibulous material or the porous membrane comprises a labeled mobilizable reagent (e.g., a detectable species as described above) that binds to or competes with the at least one analyte of interest, and wherein the labeled mobilizable reagent binds at the test zone in an amount related to the presence or amount of the analyte.

By way of example, the at least one analyte of interest may form sandwich complexes with the labeled mobilizable reagent and with reagents immobilized at the at least one test zone.

In another example, the at least one analyte of interest may compete with the labeled mobilizable reagent for binding to reagents immobilized on the least one test zone.

In certain embodiments, the labeled mobilizable reagent comprises a metal colloid label. In other embodiments, the labeled mobilizable reagent comprises a particulate label such as a fluorophore or a fluorescing or absorbing nanoparticle.

Lateral flow test devices such as those described herein can benefit from accurate positioning of the test line relative to the optical components of the integral reader. In a second aspect, the invention relates to methods of manufacturing a lateral flow test device for one or more analytes of interest, where the test device comprises a lateral flow substrate and a housing comprising a base configured to receive the lateral flow substrate and a top configured to mate with the base, comprising:

positioning a first fiducial marker comprising an optically detectable label at a location on the lateral flow substrate, wherein the optically detectable label does not participate in an assay for any analyte of interest;

positioning a second fiducial marker at a location on the housing base, wherein the second fiducial marker is a physical structure that is integral to the housing base;

inserting the lateral flow substrate into the housing base such that the first and second fiducial markers are aligned relative to one another within +/−250 µm of a predetermined orientation; and mating the optic block with the housing base, such that the precision of the optic block is within +/−75 µm of a predetermined orientation relative to the housing base.

In certain embodiments, the optically detectable label of the fiducial marker is not detectable by the device reader during the actual analyte test. In one example, the optically detectable label of the fiducial marker is functionally transparent to the electromagnetic radiation emitted from the light source (e.g., it does not absorb, reflect, or fluoresce in a manner that is detectable by the photodetector). In another example, the optically detectable label of the fiducial marker is configured to be removable from the lateral flow substrate by washing with an aqueous medium. This washing may take place either during manufacture of the test device, or during its use in an assay.

In certain embodiments, the first fiducial marker is detectable to the human eye under light of a visible wavelength, under light of an ultraviolet wavelength, and/or under light of an infrared wavelength. In preferred embodiments, the first fiducial marker is applied to the lateral flow substrate as a mixture with one or more reagents participating in the assay for an analyte of interest. In this manner, the first fiducial marker and the one or more assay reagents are colocalized on the lateral flow substrate.

As noted above, a second fiducial marker is positioned at a location on the housing base. This allows alignment of the first fiducial marker on the lateral flow strip relative to a known location on the housing base. A preferred orientation is a center-to-center alignment of the first fiducial marker and the second fiducial marker, edge detection of the first fiducial marker and the second fiducial marker, etc. The alignment may be performed using machine vision or using the human eye. The term machine vision refers to an imaging-based automatic inspection and analysis system. The alignment may also utilize a combination of imaging and human inspection in which a camera is used to image the devices and a human performs the alignment manually. This is not meant to be limiting.

In certain embodiments, the second fiducial marker comprises a groove, pit, or notch in the housing base. For example, the second fiducial marker may comprise a raised ridge in the housing base. When the second fiducial marker is a physical feature of the housing base, it may be formed during molding of the housing base, or may be formed on the housing base after molding.

Preferably, the alignment of the first fiducial marker relative to the second fiducial is within +/−125 µm of the predetermined orientation, and more preferably within +/−75 µm of the predetermined orientation.

DETAILED DESCRIPTION OF THE INVENTION

Figure 1:
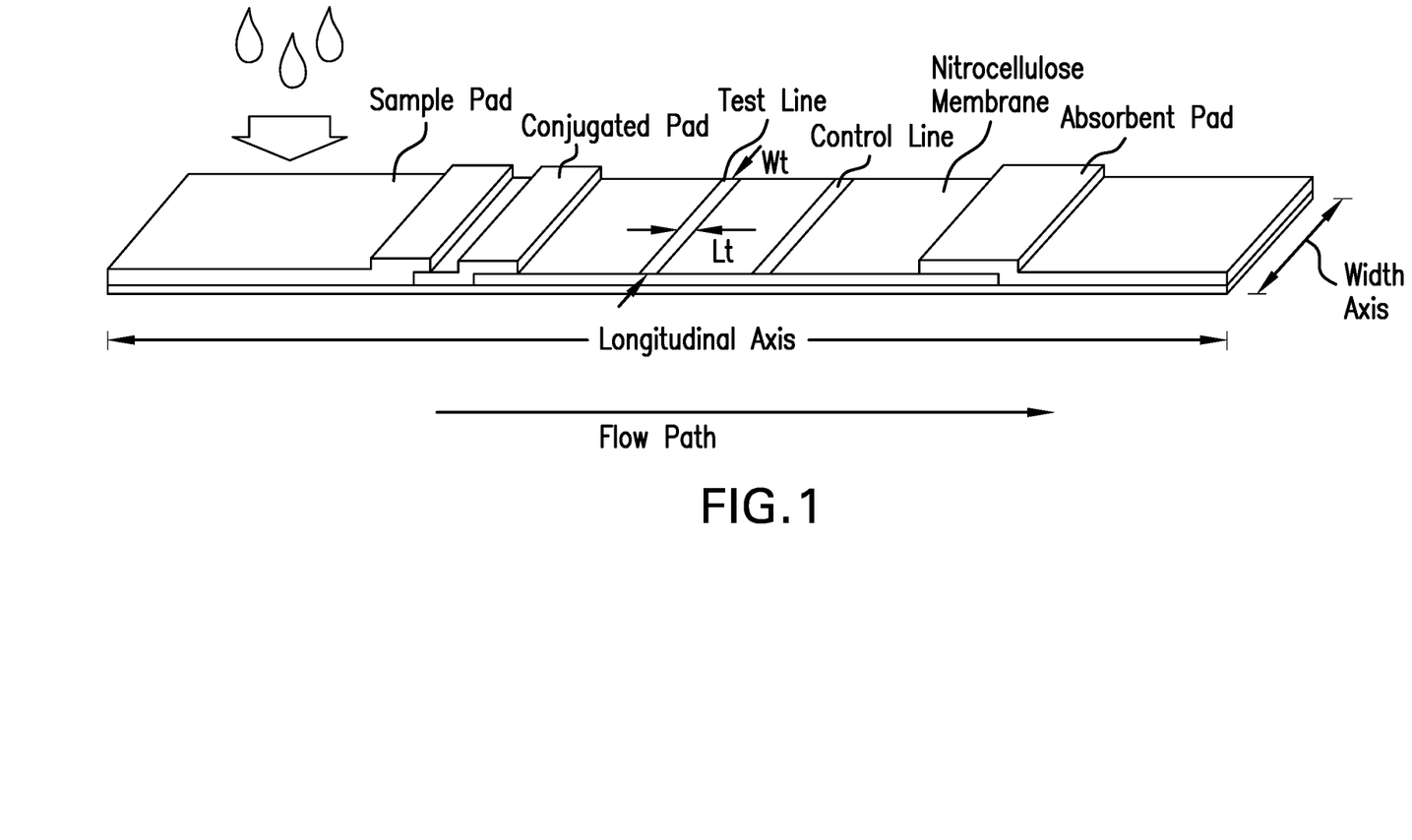
FIG. 1 depicts a typical lateral flow test strip configuration.

Lateral flow test devices have received wide acceptance in the diagnostic arts. These devices place a complicated set of reagents and manufactured elements into a simple, compact, easy to use package. See, e.g., Lateral Flow Immunoassay, Wong and Tse, eds., Humana Press, 2009. A test strip is shown in FIG. 1 in order to define certain elements of a typical test strip for use in the following discussion. A first bibulous material, often referred to as a sample pad, is provided at the proximal end of the test strip. It is this sample pad which receives the fluid sample to be tested. At the distal end of the test strip is a second bibulous material, often referred to as an absorbent pad, which operates to receive the sample fluid once it has passed through the porous membrane. The porous membrane, which may be a nitrocellulose membrane, is positioned between these two ends. The flow path of the sample is from the sample pad, through the nitrocellulose membrane, and into the absorbent pad. In doing so, the sample typically flows through a "conjugate pad", which is a portion of the device which contains a labeled reagent that binds to, or competes with, the analyte of interest. This labeled reagent is mobilized in the sample matrix so that it flows with the sample.

A test line is a location on the nitrocellulose membrane that binds the labeled reagent in an amount related to the presence or amount of the analyte of interest. While depicted as a single test line, a lateral flow test strip may have multiple test lines, each of which is used to measure the presence or amount of a different analyte. As defined herein, the test line has a width dimension $W_T$ which lies on the width axis of the test strip, and a length dimension $L_T$ which lies on the longitudinal axis of the test strip. One or more control lines are often employed to act as an environmental control and to determine if the test has been successfully performed by the test strip.

Figure 3:
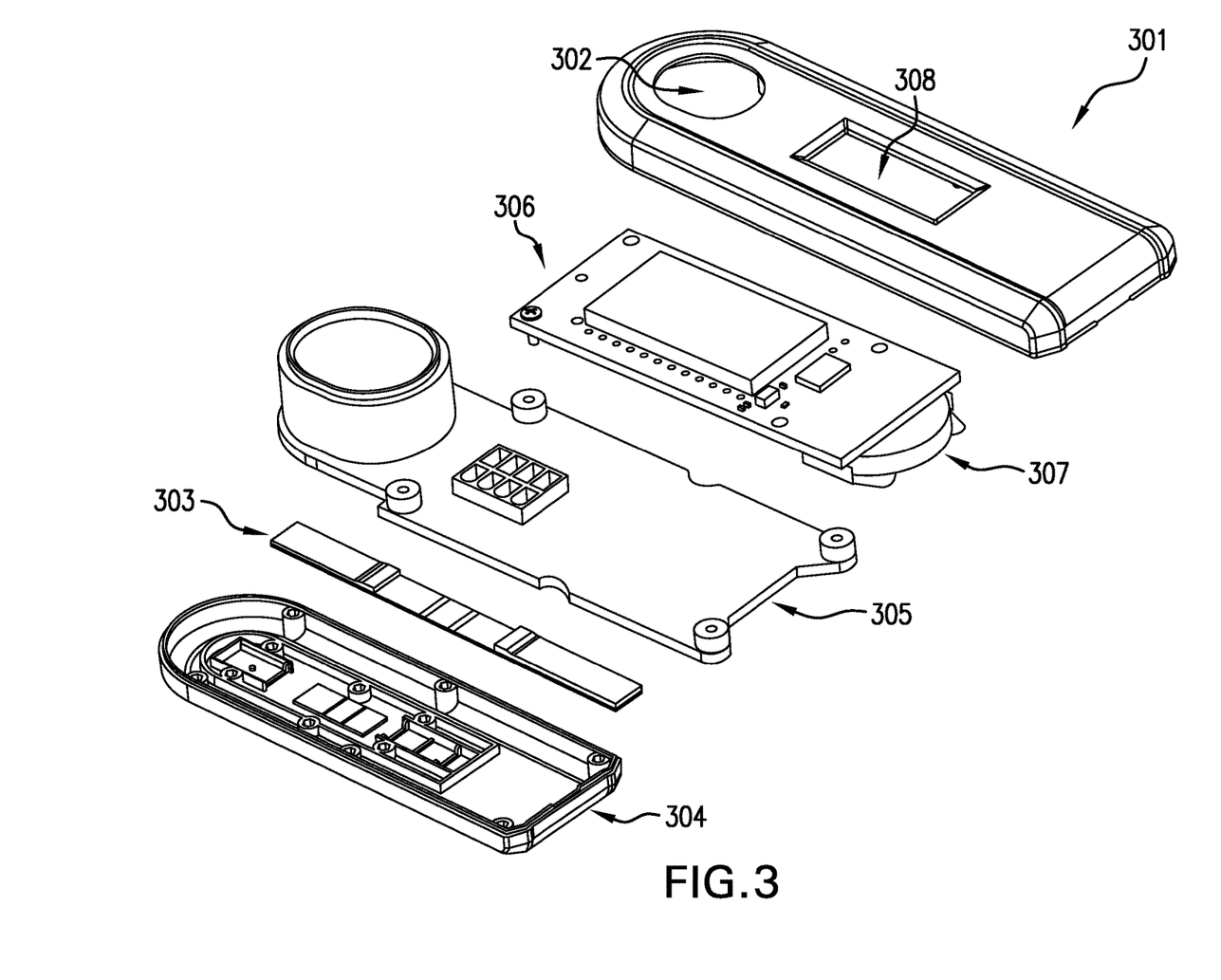
FIG. 3 depicts an exploded view of the test strip, the optic block with circuit board, and the top and bottom cartridge housing.

The test strip is typically held within a housing in order to provide protection to the test strip and for purposes of handling by the user. When the test device is read by an external reader, limited or no electronics need to be provided within the housing. In the case of an integrated reader, this housing will also provide the reader electronics necessary to read and interpret the test result. As shown in the FIG. 3, such a housing can comprise a top portion 301 having an opening 302 into which a sample may be applied. The top can be mated to a bottom portion 304 which holds the test strip 303. In the exemplary embodiment shown in FIG. 3, an optical block 305 affixed to the circuit board 306, contains the light source and photodetector and light apertures. The system is generally powered by a small battery 307 and the digital readout is displayed through the window in the top housing 308

By way of example only, a test device may be formed by introducing a moldable material into a mold assembly to form the test device lid and base; removing the test device lid and base from the mold assembly; and mating the test device lid to the test device base such that a sample receiving aperture overlies the first bibulous material and a test aperture overlies the one or more test zones. While the lid and base may be formed with discrete molds, the mold assembly may be configured as a single assembly, wherein the test device base and the test device lid are formed as a unitary part. To facilitate fit of the lid and base, the test device base and the test device lid may be formed as a unitary part connected by one or more flexible hinge regions (e.g. living hinges) configured to allow the test device lid to mate to the test device base.

The skilled artisan will understand that a number of polymers may be used to form the test device base, including thermoplastics, some thermosets, and elastomers. Common thermoplastics include PMMA, cyclic olefin copolymer, ethylene vinyl acetate, polyacrylate, polyaryletherketone, polybutadiene, polycarbonate, polyester, polyetherimide, polysulfone, nylon, polyethylene, and polystyrene. Common thermosets include polyesters, polyurethanes, duroplast, epoxy resins, and polyimides. This list is not meant to be limiting. Functional filler materials such as talc and carbon fibers can be included for purposes of improving stiffness, working temperatures, and part shrinkage.

Figure 2:
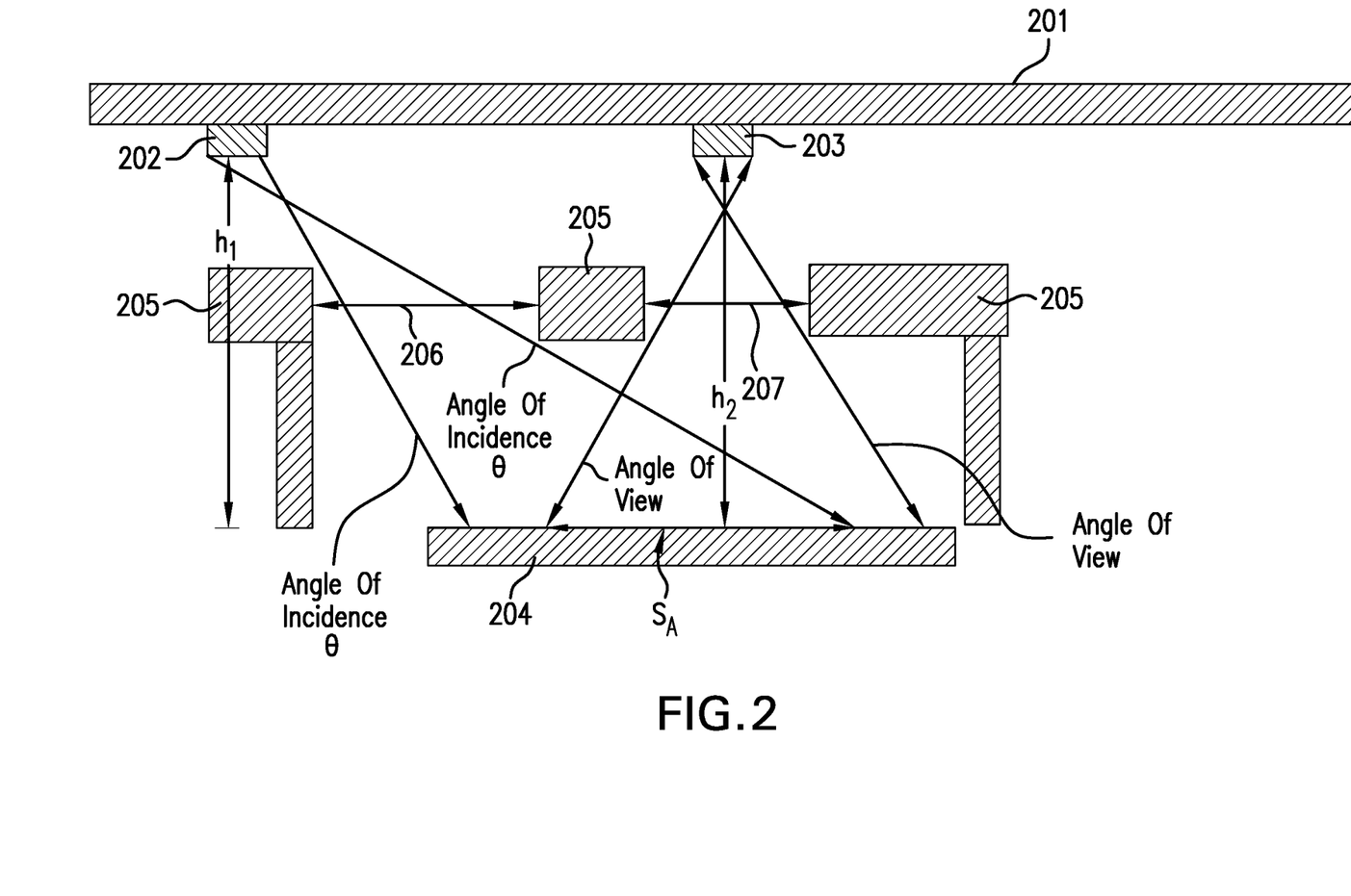
FIG. 2 depicts a cross section along the width axis at the location of the aperture.

FIG. 2 depicts a cross section along the width axis ($W_T$) at the point of a test or control line position along the longitudinal axis (LT) showing the arrangement of the optical block of a test device of the present invention. In this schematic view, the test device lid and base are not shown. A circuit board 201 supports a light source 202 and a photodetector 203. The test strip 204 is shown along its width axis $W_T$ such that light from the light source 202 passes through aperture 206 in optic block 205 (see 305 in FIG. 2) in order to illuminate the test line with an angle of incidence θ. The light source 202 is offset laterally from the center of the test line in order to minimize specular reflection of the incident light from reaching photodetector 203. The area of the test line that is illuminated is determined by the height $h_1$ and the dimensions of aperture 206, and is configured to limit illumination to the test line area, with minimal overlap onto portions of the lateral flow membrane that do not contain the test line. Preferably, the area of the lateral flow membrane that is illuminated is no more than 50% larger than $W_T$, and no more than 50% larger than $L_T$, and is more preferably no more than 25%, or 10% larger than $W_T$ and $L_T$, respectively. This is in order to minimize reflection of non-relevant incident light received by photodetector 203. Furthermore, the illuminated width, $W_T$, may be actually be less than $W_T$ in order to avoid illuminating anything but the test strip.

A second aperture 207 in support 205 and height $h_2$ define the sampling area $S_A$, which is the area of the lateral flow test strip that is viewed by photodetector 203. The aperture dimension and $h_2$ are defined to that sampling area $S_A$ is no more than 2× the area occupied by the test line. Preferably, $S_A$ is defined by a sampling width ($W_S$) that is no more than 0% larger than $W_T$, and a sampling length ($L_S$) that is no more than 50% larger than $L_T$, and is more preferably no more than 25% greater than $L_T$, or 90% of $W_T$.

Figure 4:
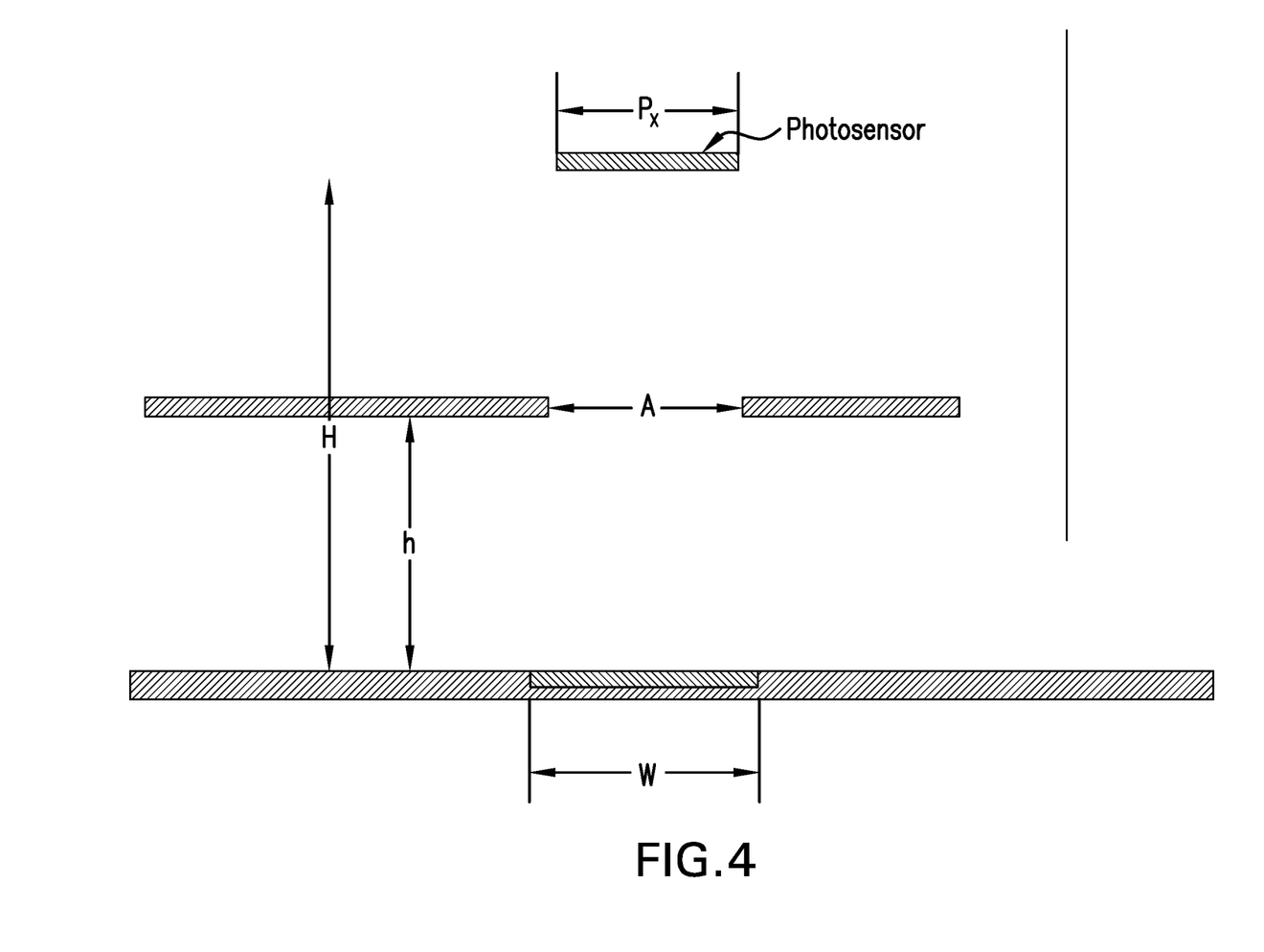
FIG. 4 depicts a cross section along the longitudinal axis at the location of the $2^{nd}$ aperture and test line along the test strip.

FIG. 4 depicts a longitudinal cross section of a single photodetector in alignment with a test line. The purpose of the aperture in this direction is to define the extent of the longitudinal viewing cone. In this figure The aperture width A may be defined by the equation $A<(h/H)*(Px-3W)+3W$, where:

Px=X dim (width) of Photosensor
W=X dim (width) of developed assay line
h=height from top of strip to limiting stop of aperture
H=height from top of strip to bottom of photosensor
A=width of defining aperture.

Figure 5:
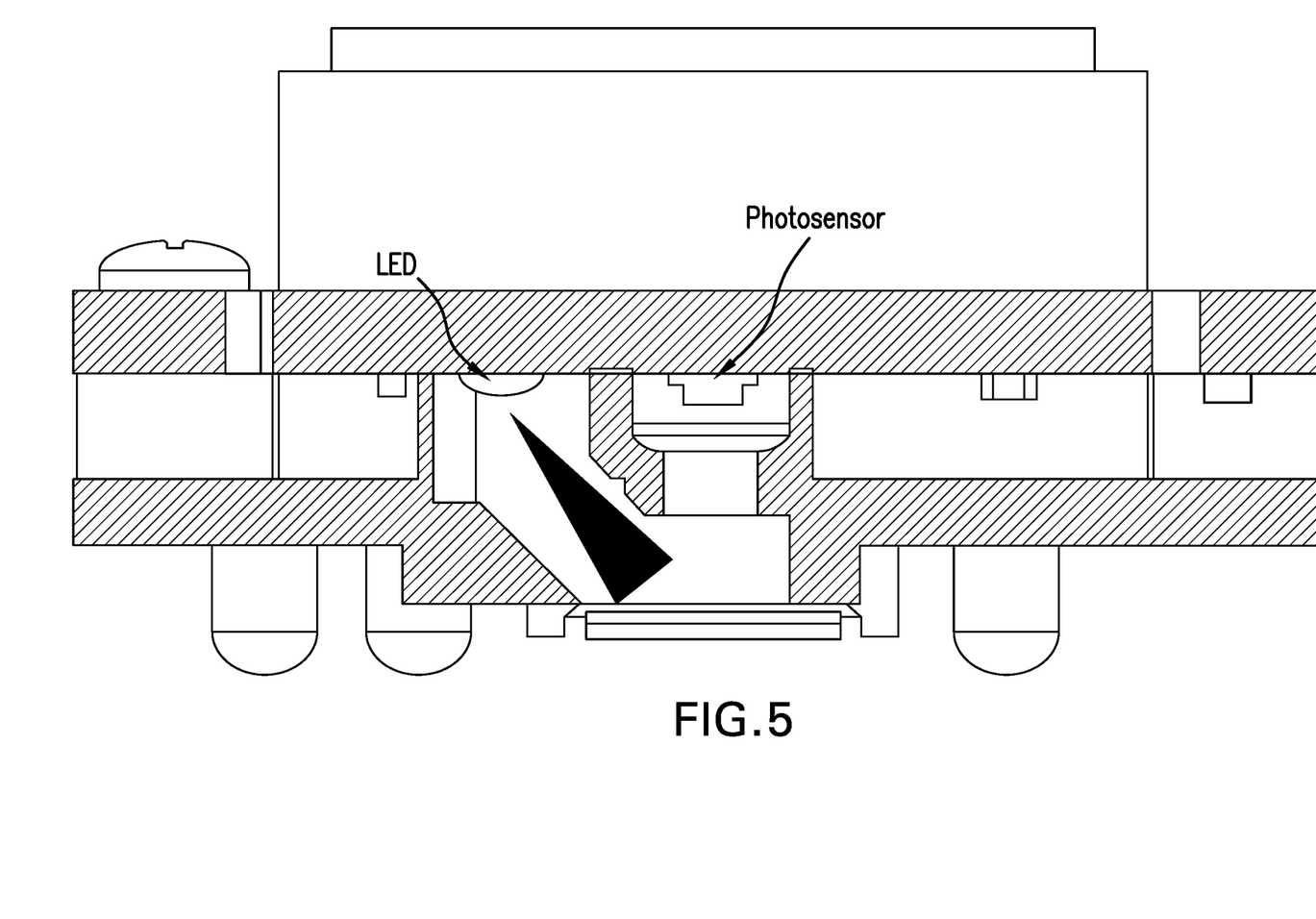
FIG. 5 depicts a cross section along the width axis at the location of a test line.

This equation is an approximation and may vary if refractive materials, such as a lens, filter, or plastic coating are in the optical path. FIG. 5 depicts a cross-section along the width axis of an exemplary lateral flow test device of the present invention at the level of a test zone, depicting the light source as a light emitting diode illuminating a test device through an elongate aperture, and the photodetector positioned above the test line to interrogate the test line upon illumination.

Figure 6:
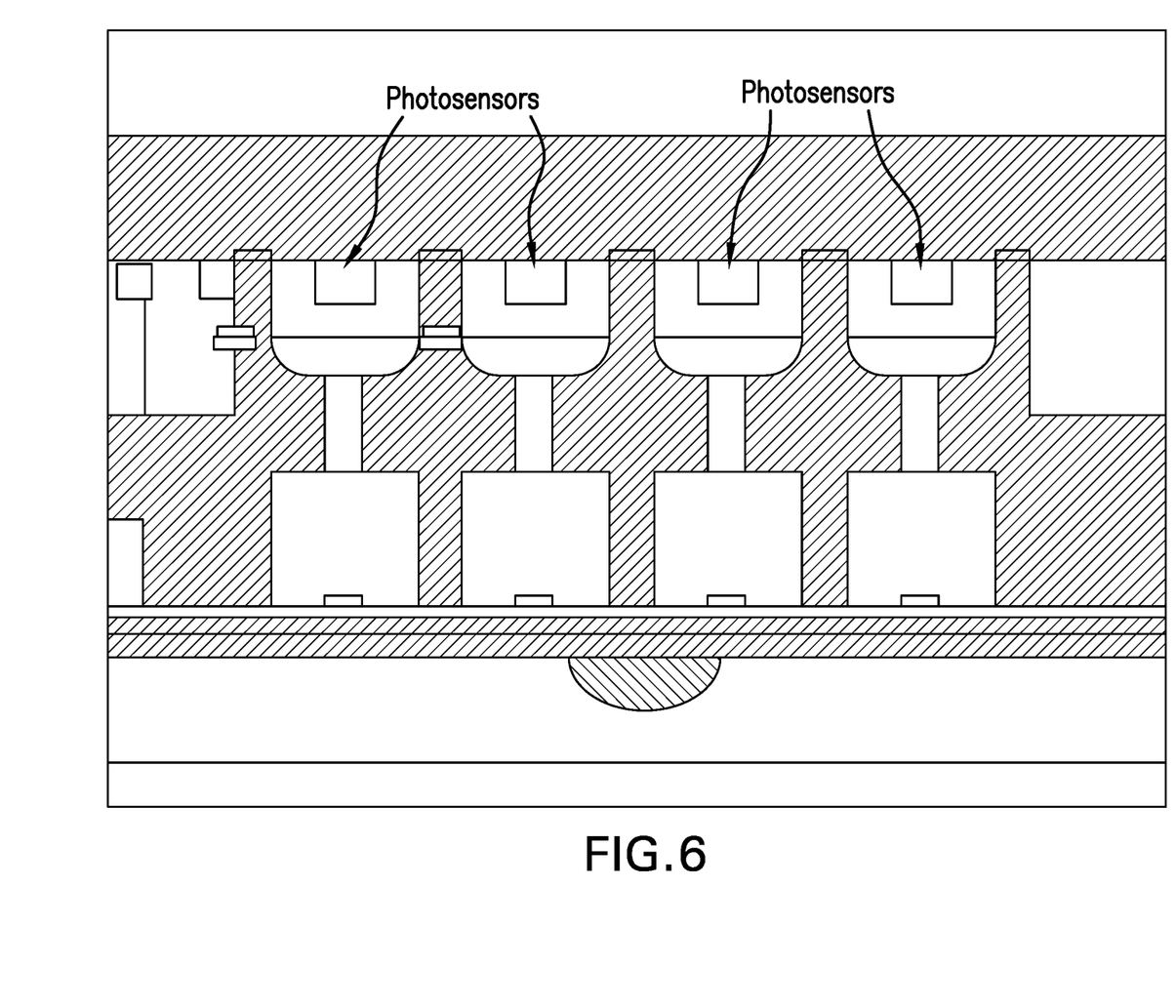
FIG. 6 depicts a cross section along the length axis across multiple aperture 2 locations.

FIG. 6 depicts a cross-section along the longitudinal axis of an exemplary lateral flow test device of the present invention showing multiple separate test zones and multiple photodetectors. The height between the photodetector and light source is defined their relative positions on the optic block. The height of the optic block to the test strip is defined by a set of "legs" that reach down to bottom enclosure. This height is a critical parameter that must be maintained to ensure a consistent illumination and viewing region from one device to the next. The legs may be formed as an integral part of the optic block, but could be separate legs which are affixed to the optic block or circuit board.

Figure 7:
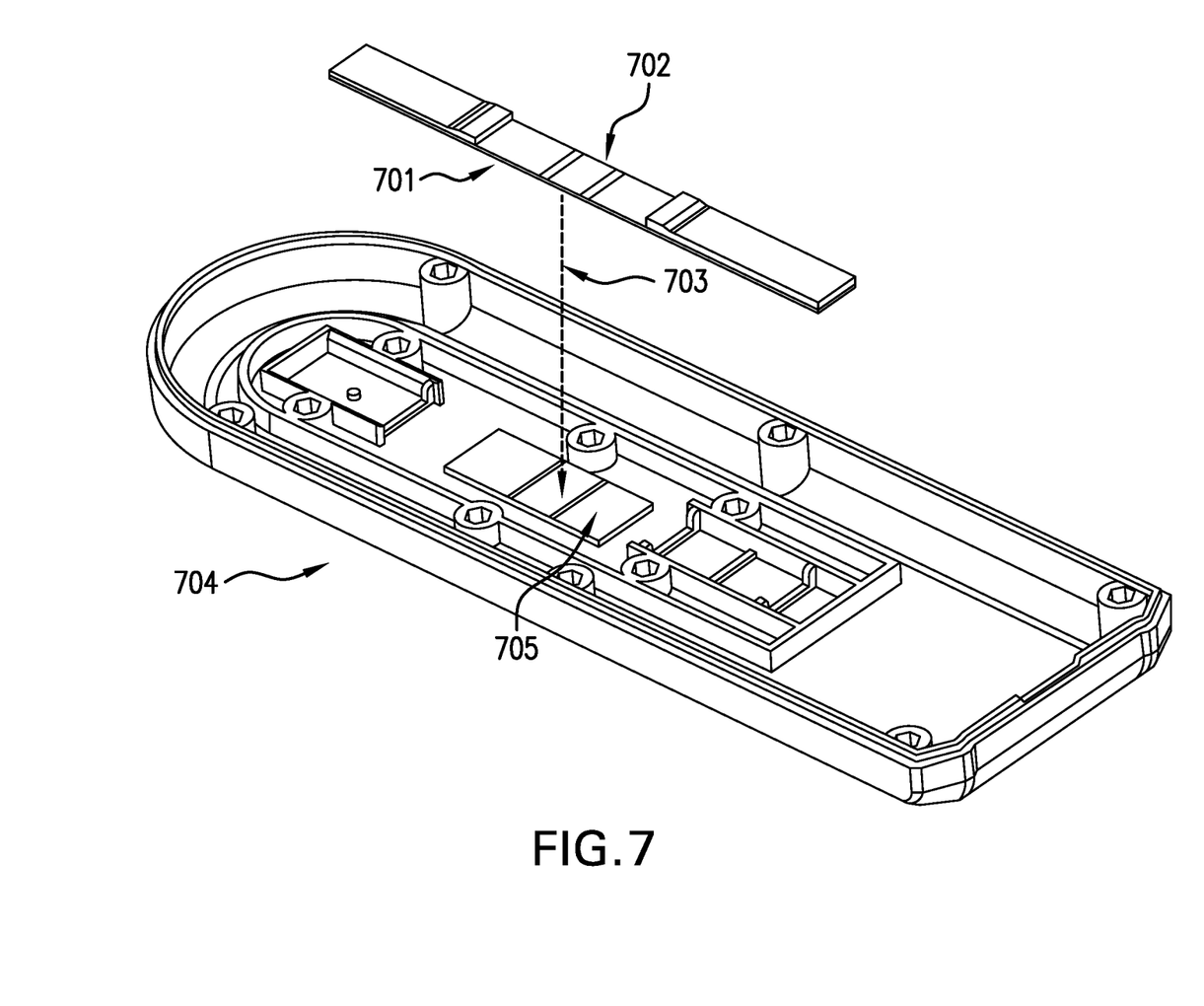
FIG. 7 depicts the features used to align the test strip to the housing base.

FIG. 7 Depicts the positioning of the lateral flow strip with respect to the base. The test strip 701 is aligned to the housing base 704 by matching the fiducial within the control or test line 702 with a fiducial marked on the housing base 705. The alignment correspondence is shown via the dotted line 703.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A lateral flow analyte test device comprising:
   (a) a test strip comprising:
      a first bibulous material defining a sample receiving region;
      a second bibulous material defining an absorbent region; and
      a porous membrane comprising:
         at least one test zone comprising one or more reagents;
         a proximal end and a distal end;
         a first lateral edge and a second lateral edge;
         a first length defined from the proximal end to the distal end and a first width defined from the first lateral edge to the second lateral edge wherein the first length is perpendicular to the first width; and
         a porous membrane surface defined by the first length and the first width to the first length, wherein the first bibulous material is disposed at the proximal end, the second bibulous material is disposed at the distal end, the first bibulous material and the second bibulous material are fluidically connected to the porous membrane, the porous membrane is configured to enable a sample applied to the sample receiving region to traverse from the proximal end to the distal end, and the at least one test zone is configured to bind at least one analyte of interest from the sample and immobilize the at least one analyte of interest at the at least one test zone, the at least one test zone having a second width defined along the first width and a second length defined along the first length;
   (b) a substantially rigid base supporting the test strip;
   (c) a circuit board comprising:
      at least one light source configured to illuminate the at least one test zone with electromagnetic radiation, and
      at least one photodetector configured to detect one or more optical signals from the at least one test zone illuminated by the at least one light source;
   (d) a circuit board support comprising:
      a first aperture having a first end proximal to the at least one light source and a second end a second end proximal to the at least one test zone; and
      a second aperture, wherein the circuit board is configured to (i) position the at least one light source above the at least one test zone at a first height location lateral to the first width, and to (ii) position the at least one photodetector above the at least one test zone at a second height location approximately centered on the first width wherein the first aperture is elongate and is configured to enable electromagnetic radiation from the light source disposed at the first height to illuminate the at least one test zone at an incidence angle between about 40° and about 10° relative to a line perpendicular to the porous membrane surface and wherein the second aperture is disposed between the at least one test zone and the at least one photodetector, and is configured to limit a view angle for the at least one photodetector to a porous membrane area including the at least one test zone and comprising less than twice an area range equivalent to the at least one test zone;
   (e) a processor operably connected to the at least one light source and to the at least one photodetector and configured to:
      (i) control illumination of the at least one test zone by the at least one light source,
      (ii) receive an electrical signal from the at least one photodetector based on the one or more optical signals, and
      (iii) convert the electrical signal into an assay result signal indicative of a presence or of an amount of the at least one analyte of interest in the sample; and
   (f) a display operably connected to the processor and configured to receive the assay result signal from the processor and to display an assay result based on the assay result signal.

2. The lateral flow analyte test device according to claim 1 wherein the one or more optical signals detected from the at least one test zone by the at least one photodetector is defined by: 1-[(a run-time optical signal)−(an offset signal)]/[(a reference signal)−(the offset signal)], wherein the run-time optical signal is one or more optical signals measured in a test run; the reference signal is measured from a given measurement zone; the reference signal is an optical signal measured from a corresponding lateral flow analyte test device unreacted with a sample; and the offset signal is an optical signal measured from a corresponding lateral flow analyte test device having a porous membrane having a material absorbing at least 90% of electromagnetic radiation emitted from the at least one light source.

3. The lateral flow analyte test device according to claim 2 wherein the assay result is a quantitative result.

4. The lateral flow analyte test device according to claim 3 wherein the amount of the at least one analyte of interest in the sample is measured based on a change in absorbance or based on a change in fluorescence of electromagnetic radiation emitted by the light source and incident on the at least one test zone.

5. The lateral flow analyte test device according to claim 1 wherein the porous membrane area is defined by a sampling width, and a sampling length wherein the sampling width is less than 1.5 times the first width and the sampling length is less than 1.5 times the first length.

6. The lateral flow analyte test device according to claim 1 wherein the porous membrane area is defined by a sampling width, and a sampling length wherein the sampling width is less 1.9 times the first width and the sampling length is less than 1.1 times the first length.

7. The lateral flow analyte test device according to claim 1 wherein the second aperture is configured to prevent light not emanating from the test strip from impinging on the at least one photodetector.

8. The lateral flow analyte test device according to claim 1 wherein the first aperture, the light source, the second aperture and the at least one photodetector are configured to prevent incident light reflecting off of the test strip from impinging into the at least one photodetector.

9. The lateral flow analyte test device according to claim 1, wherein the first bibulous material or the porous membrane comprises a labeled mobilizable reagent for binding to the at least one analyte of interest, and wherein the labeled mobilizable reagent and the at least one analyte of interest can form sandwich complexes with the one or more reagents.

10. The lateral flow analyte test device according to claim 1 wherein the first bibulous material or the porous membrane comprises a labeled mobilizable reagent for competing with the at least one analyte of interest to bind to the one or more reagents.

11. The lateral flow analyte test device according to claim 9 wherein the labeled mobilizable reagent comprises a metal colloid label.

12. The lateral flow analyte test device according to claim 9 wherein the labeled mobilizable reagent comprises a particulate label.

13. The lateral flow analyte test device according to claim 9 wherein the labeled mobilizable reagent comprises a fluorescent label.

14. The lateral flow analyte test device according to claim 10 wherein the labeled mobilizable reagent comprises a metal colloid label.

15. The lateral flow analyte test device according to claim 10 wherein the labeled mobilizable reagent comprises a particulate label.

16. The lateral flow analyte test device according to claim 10 wherein the labeled mobilizable reagent comprises a fluorescent label.

* * * * *